United States Patent [19]

Spielvogel et al.

[11] Patent Number: 4,587,359
[45] Date of Patent: May 6, 1986

[54] AMINE-CARBAMOYLBORANE ADDUCTS

[75] Inventors: Bernard F. Spielvogel, Raleigh; Andrew T. McPhail, Durham; Iris H. Hall, Chapel Hill, all of N.C.

[73] Assignee: The United States of America as represented by the Secrtary of the Army, Washington, D.C.

[21] Appl. No.: 611,247

[22] Filed: May 17, 1984

[51] Int. Cl.⁴ ................................................ C07F 5/02
[52] U.S. Cl. ........................................... 564/8; 564/9
[58] Field of Search ....................................... 564/8, 9

[56] References Cited

U.S. PATENT DOCUMENTS 4,368,194  1/1983  Spielvogel et al. ................. 424/185

Primary Examiner—Anton H. Sutto
Assistant Examiner—R. A. Picard
Attorney, Agent, or Firm—Damian Porcari; John H. Raubitschek; Peter A. Taucher

[57] ABSTRACT

This invention involves amine-carbamoylborane compounds of the formula $R_1R_2NH \cdot BH_2C(O)NHR_3$ wherein $R_1$ and $R_2$ are hydrogen or certain alkyl moieties and $R_3$ is an alkyl. A process for their preparation involving an amine displacement reaction is also described. A method of use and pharmaceutical compositions containing the subject compounds are also described.

8 Claims, No Drawings

AMINE-CARBAMOYLBORANE ADDUCTS

BACKGROUND OF THE INVENTION

Trimethylamine-(ethylcarbamoyl)borane, $Me_3N.BH_2C(O)NHEt$, is a precursor in the synthesis of $Me_3N.BH_2COOH$, the protonated boron analogue of the dipolar amino acid betaine $^+Me_3NCH_2COO^-$. Both $Me_3N.BH_2COOH$ and its ethylcarbamoyl derivative have demonstrated significant antitumor and antihyperlipidemic activity in mice. B. F. Spielvogel et al., Am. Chem. Soc., 93, p. 5702 (1976); I. H. Hall et al., J. Pharm. Sci., 68, p. 685 (1979) and I. H. Hall et al., J. Pharm. Sci., 70, p. 339 (1981). Also, the trimethylamine-(ethylcarbamoyl)borane showed significant antiinflammatory and antiarthritic activities in animal model studies. I. H. Hall et al., J. Pharm. Sci., 69, p. 1025 (1980) Because of their potential biological activities the preparation of the remaining amine members was undertaken. Related organoborane technology is disclosed in U.S. Pat. No. 4,209,510; No. 4,312,980 and No. 4,368,194.

SUMMARY OF THE INVENTION

This invention is directed to amine-carbamoylborane compounds of the formula $$R_1R_2NH.BH_2C(O)NHR_3$$

wherein $R_1$ and $R_2$ are selected from the moieties hydrogen and the lower alkyl members having a straight or branched chain up to $C_8$ including methyl, ethyl, propyl and n-butyl, and wherein $R_3$ is a lower alkyl member having a straight or branched chain up to $C_8$ including methyl, ethyl, propyl or n-butyl. Preferred are the lower methyl or ethyl moieties which minimize synthesis problems due to steric hindrance involving the larger or branched chain moieties.

Aspects of this invention also include a process for the preparation by amine displacement of the compounds of this invention as well as pharmaceutical compositions containing a subject compound. An additional aspect of this invention relates to a method for the treatment of tumor tissue in an animal comprising the therapeutic use of an antineoplastic or tumor growth inhibiting amount of a compound of this invention. The compounds of this invention, considered to be boron analogues of amino acid amides, are also of interest as simple models of a (boron amino acid) peptide linkage.

DESCRIPTION OF THE INVENTION

The preparation of the compounds of this invention are exemplified by reference to the following experimental procedures which describe reaction conditions which yield (ethylcarbamoyl)borane adducts.

A series of (ethylcarbamoyl)borane adducts of different amines and $NH_3$ were prepared according to Scheme I.

Scheme I $$Me_3N.HCl + NaBH_3CN \xrightarrow{THF^a} Me_3N.BH_2CN \xrightarrow{(C_2H_5)_3OBF_4{}^b}$$

$$Me_3N.BH_2CNC_2H_5{}^+BF_4{}^- \xrightarrow{1N\ NaOH^c}$$

$$Me_3N.BH_2C(O)NHC_2H_5 \xrightarrow{RR'NH^d}$$

-continued
Scheme I $$RR'NH.BH_2C(O)NHC_2H_5$$
2, R = CH$_3$, R' = CH$_3$
3, R = CH$_3$, R' = H
4, R = H, R' = H

[a]Reflux (66° C.) for 48 hours
[b]Reflux (45° C.) in CH$_2$Cl$_2$ for 24 hours
[c]Stirring (0° C.) until basic
[d]Room temperature (25° C.) for ca. 1 week The parent compound 1, trimethylamine-(ethylcarbamoyl)borane was prepared as previously described in B. F. Spielvogel et al., J. Am. Chem. Soc., 98 p. 5702 (1976) and I. H. Hall et al., J. Pharm. Sci., 68, p. 685 (1979) by refluxing (under dry $N_2$) a solution of $Me_3N.BH_2CN$ in $CH_2Cl_2$ with 2 equivalents of triethyloxonium tetrafluoroborate for 24 hours. The compounds $Me_3N.BH_2CN$ and triethyloxonium tetrafluoroborate are referred to in P. Wisian-Neilson et al., Inorg. Chem. 17, p. 2327 (1978) and H. Meerwein, Org. Synth., 46, p. 113 (1966), respectively. The resulting ethylnitrilium salt (not isolated) was hydrolyzed at 0° C. with 1N NaOH until basic and finally purified by vacuum distillation, giving a 75% yield. Dimethylamine-(ethylcarbamoyl)borane was made from 1 by a $(CH_3)_2NH$-exchange reaction in a pressure-glass vessel at room temperature for 8 days, and ca. 80% conversion (by $^1H$ NMR) was obtained. Longer reaction periods (2–3 weeks) gave similar results. Amide 2 is readily purified by washing a $CH_2Cl_2$ solution of the crude mixture with a small quantity of water whereby 1 is removed. The bulk $CH_2Cl_2$ solution containing the product was dried, and rotary evaporation of the solvent gave 78% yield. Finally, the product was distilled under reduced pressure to get an analytical sample. The trimethylamine(ethylcarbamoyl)borane and its dimethylamine analogue are thermally unstable at higher temperature ($>100°$ C.) and undergo considerable decomposition when subjected to vacuum distillation at oil-bath temperatures $>100°$ C. The methylamine-(ethylcarbamoyl)borane and ammonia-(ethylcarbamoyl)borane were similarly prepared from 1 by exchange reactions with $CH_3NH_2$ and $NH_3$, respectively, in a glass pressure reaction vessel at room temperature for 1 week. The crude amide was purified by recrystallization from $CH_2Cl_2$/pentane, giving a 65% yield, whereas the ammonia analogue was recrystallized from distilled water, giving a 60% yield.

All of the compounds were characterized by elemental analyses, and IR, $^1H$, $^{11}B$, and $^{13}C$ NMR spectroscopy. The physical and spectral data of these amides are given in Table I.

TABLE 1

Physical and Spectroscopic Data for Amino-(Ethylcarbamoyl)boranes

| Compound | bp or mp, °C. (P, torr) | % yield | $^{11}B$ NMR data,$^a\delta$ | $J_{B-H}$ Hz |
|---|---|---|---|---|
| Me$_3$N.BH$_2$CONHEt (1) | 80 (0.15) | 75 | −7.40 | 90 |
| Me$_2$NH.BH$_2$CONHet (2) | 110–112 (0.2) | 77 | −11.55 | 88 |
| MeNH$_2$.BH$_2$CONHEt (3) | 99–110 | 65 | −15.37 | 84 |
| NH$_3$.BH$_2$CONHEt (4) | 125–126 | 60 | −19.59 | 80 |

BE$_3$.Et$_2$O was used as an external standard, and the chemical shifts shown were negative upfield from the standard.

The IR spectra exhibited characteristic B—H, and C=O absorptions. The $^1H$, $^{11}B$, and $^{13}C$ NMR spectral data were consistent with the structures of these compounds.

EXPERIMENTAL SECTION

General Procedures. IR spectra were recorded on a Perkin-Elmer 297 spectrometer. Solid samples were prepared as Nujol mulls between NaCl disks; oils were recorded neat. Proton NMR spectra were obtained on Varian EM 360A or JEOL-FX 90Q spectrometers. Carbon and boron NMR spectra were obtained on a JEOL-FX 90Q spectrometer. Elemental analyses were performed by Galbraith Laboratories, Inc., Knoxville, TN, and M-H-W Laboratories, Phoenix, AZ. The following compounds were purchased and used without further purification: $(CH_3)_3N.HCl$ (Aldrich), $NaBH_3CN$ (Aldrich), $(CH_3)_2NH$ (Eastman Kodak), $CH_3NH_2$ (Union Carbide), $NH$ (Matheson). $(C_2H_3)_3OBF_4$ solution was either purchased (Aldrich) or made by the known method of H. Meerwein, supra; the same synthetic method is considered applicable to the other alkylated oxonium tetrafluoroborates. $(CH_3)_3N.BH_2CN$ was prepared from $(CH_3)_3N.HCl$ and $NaBH_3CN$. The amine-exchange reactions were carried out in 250-mL glass pressure reaction vessels. The pressure reaction vessels and their safety shields were purchased from Lab-Crest Scientific Co., Warminster, PA. Although the $NH_3$ exchange has been carried out in the glass vessel without incident, the use of stainless-steel vessels is greatly preferred for safety.

Trimethylamine-(Ethylcarbamoyl)borane (1). A solution of trimethylamine-cyanoborane (11.9 g, 0.12 mol) and 250 mL of 1M $Et_3OBF_4$ in $CH_2Cl_2$ (0.25 mol) was refluxed under nitrogen for 24 hours. The reaction mixture was cooled to 0° C., and 1N NaOH was added slowly with vigorous stirring until the solution was basic (pH~8). After the mixture was stirred 1 hour at room temperature, the organic layer was separated and the aqueous layer was extracted three times with $CH_2Cl_2$. The organic portions were combined and dried over $MgSO_4$ and the solvent was removed in vacuo. The remaining viscous liquid was distilled under vacuum with minimum heating to give 1; 13.1 g (75%); bp 80° C. (0.15 torr); IR (neat) 3289 ($\nu(NH)$), 2915 ($\nu(CH)$), 2330 ($\nu(B-H)$), 1590 (amide I), 1480 (amide II) cm$^{-1}$; $^1HNMR(CDCl_3)\delta1.07$ (t,$CH_3CH_2$), 2.75 (s, $CH_3N$), 3.57 (m, $CH_2CH_3$), 5.43 (br s, NH); $^{13}CNMR(CDCl_3)$ $\delta$ 15.3 ($CH_3CH_2$), 31.5 ($CH_2CH_3$), 51.8 ($CH_3N$), 182.8 (CO); $^{11}BNMR(CDCl_3)$ $\delta$ −7.4 (1:2:1 t, J=90 Hz). Anal. Calcd for $C_6H_{17}BN_2O$; C, 50.10; H, 11.83; N, b 19.49; B, 7.45. Found: C, 49.86; H, 11.69; N, 1959; B, 7.50.

Dimethylamine-(Ethylcarbamoyl)borane (2). Anhydrous $(CH_3)_2NH$ (50 g, 1.1 mol) was cooled to 0° C. and poured into the glass pressure vessel containing 1 (14.38 g, 0.1 mol) kept at 0° C. The vessel was assembled and kept at room temperature for 8½ days with occasional shaking each day. The reaction vessel was then cooled to 0° C. and slowly opened. To this solution was added ca. 8 mL of pentane, and the volatile amines were allowed to evaporate off. The remaining amines and solvent were removed by rotary evaporation. A pale yellow liquid was obtained that had ca. 21% unreacted 1 (by proton NMR). The mixture was taken up in $CH_2Cl_2$ and washed once with water. The water washing was repeatedly extracted with $CH_2Cl_2$ and the proton NMR spectrum of the $CH_2Cl_2$ showed that it contained only the starting amide (1). The $CH_2Cl_2$ solution containing the product, uncontaminated by 1 (by proton NMR), was dried over $MgSO_4$ and treated with charcoal. The solvent was then removed by rotary evaportation (and the pale yellow oil (10.1 g (77.7%)) was vacuum distilled: bp 110°-112° C. (0.2 torr); IR ($CH_2Cl_2$) 3440 ($\nu(NH)$), 2965 ($\nu(CH)$), 2365 ($\nu(BH)$), 1590 (amide I), 1490 (amide II) cm$^{-1}$, $^1HNMR(CDCl_3)$ $\delta$ 1.06 (t, $CH_3CH_2$), 2.40 (d, $CH_3N$), 3.18 (m, $CH_2CH_3$), 5.80 (br s, amine H), 6.45 (br s, amide H); $^{11}BNMR$ ($CDCl_3$, $BF_3Et_2O$)-11.55 (t, $J_{B-H}$=88 HZ); $^{13}C$ NMR ($CDCl_3$) 15.26 ($CH_3CH_2$, 32.33 ($CH_2CH_3$), 42.91 ($CH_3N$). Anal. Calcd for $C_3H_{15}BN_2O$: C, 46.20; H, 11.63; N 21.55. Found: C, 45.94; H, 11.58; N, 21.30.

Methylamine-(ethylcarbamoyl)borane (3). Anhydrous methylamine was condensed (ca. 30 mL) at −78° C. from the gas cylinder and transferred to the glass pressure reaction vessel containing 2.86 g (19.85 mmol) of 1 already cooled to −78° C. The pressure reaction vessel was then assembled and slowly allowed to warm to room temperature and kept for 1 week with occasional shaking. The reaction vessel was then cooled to −78° C. and carefully opened. To this solution was added ca. 100 mL of pentane, and excess amines were allowed to evaporate off at room temperature. Some solid product separated, and the remaining solvent and was removed by rotary evaporation. The crude product was dissolved in $CH_2Cl_2$ (ca. 200 mL) and filtered into n-pentane. An off-white solid (0.9 g) separated. To the filtrate was added additional pentane, and 0.57 g of more product was obtained. The combined solid (1.49 g (65%)) was recrystallized from $CH_2Cl_2$/pentane: mp 99-100 C; IR (Nujol) 3330 ($\nu(NH)$), 3120 ($\nu(CH)$), 2380 ($\nu(BH)$), 1620 (amide), 1570 (m, amide) cm$^{-1}$; $^1HNMR(CDCl_3)$ 1.09 (1, $CH_3CH_2$), 2.43 (t, MeN), 3.23 (m, $CH_2CH_3$), 4.95 (br s, amide H); $^{13}CNMR(CDCl_3)$ $\delta$ 15.20 ($CH_3CH_2$), 32.20 ($CH_2CH_3$), 32.36 ($Me_3M$); $^{11}BNMR(CDCl_3, BF_3$ $Et_2O)$ $\delta$ −15.37 (J=84 Hz). Anal. Calcd for $C_4H_{13}N_2BO$: C, 41.43; H, 11.30; N, 24.16. Found: C, 41.20; H, 11.07; N, 24.03.

Ammonia-(ethylcarbamoyl)borane (4). Anhydrous $NH_3$ was condensed at −78° C. from the gas cylinder and ca. 40 mL of liquid $NH_3$ transferred to the glass pressure reaction vessel containing 1.48 g (10.20 mmol) of that was previously cooled to −78° C. The reaction vessel was then assembled, allowed to warm to room temperature, and kept for 1 week with occasional shaking each day. The reaction vessel was then cooled to −78 C. and slowly opened. The excess $NH_3$ and amines were allowed to evaporate off at room temperature, ca. 200 mL of $CH_2Cl_2$ was added to the vessel, and the resultant mixture was filtered. The solution was kept in the refrigerator, and fluffy crystals formed. The crude product was recrystallized from doubly distilled water. The white needles (4) (0.62 g (60%) mp 125°-126° C.) had the following spectral properties: IR (Nujol) 3350 ($\nu(NH)$), 3270 ($\nu(CH)$), 2340 ($\nu(BH)$), 1620 (amide I), 1550 (amide II) cm$^{-1}$; $^1HNMR(D_2O)$ 1.06 (t, $CH_3CH_2$), 3.15 (q. $CH_2CH_3$); $^{13}CNMR(D_2O)$ $\delta$ 16.60 ($CH_3CH_2$), 35.22 ($CH_2CH_3$); $^{11}BNMR(D_2O, BF_3.EtO)$ $\delta$ −19.59=80 Hz). Anal. Calcd for $C_3H_{11}N_2BO$: C, 35.35; H, 10.88; N, 27.48. Found: C, 35, 82; H, 10.86; N, 27.72.

Synthesis of additional compounds such as the (ethylcarbamoyl)borane adducts with a desired amine and the reactant trimethylamine-(ethylcarbamoyl)borane by the amine displacement reaction described above with regard to the exemplary adducts is considered to be evident to the skilled artisan in view of the experimental procedures described above or their obvious variants. It is to be noted that the only known procedure for the synthesis of the compounds of this invention, in contradistinction to the trimethylamine reactant species, is the subject amine displacement reaction.

Use of compounds according to this invention in Ehrlich Ascites tumor screens for antineoplastic activity has been investigated.

CF male mice (~25 g) were inoculated intraperitoneally on day 0 with $2 \times 10^6$ Ehrlich ascites cells. Compositions containing compounds of this invention were prepared in 0.05% polysorbate 80 by homogenation and injected intraperitoneally on days 1-9 at 20 mg/kg/day. On day 10, the mice were sacrificed and the cells from the peritoneal cavity harvested. The total ascites tumor and packed cell (ascrit) volumes were determined and used to calculate the percent inhibition according to the procedure described in C. Piantadosi et al., *J. Pharm. Sci.*, 58, p. 821 (1969). The compound MeNH$_2$.BH$_2$.C(O)NHEt provided 91% inhibition and Me$_2$NH.BH$_2$.C(O)NHEt provided 72.2% inhibition. Mercaptopurine and mephalan were used as positive controls in the screen. Other pharmaceutically acceptable carriers, diluents, adjuvants or dosages are readily ascertainable by the skilled artisan.

In a tissue distribution study relating to treatment of tumor tissue in an animal by boron neutron capture therapy, a representative compound of this invention MeNH$_2$.BH$_2$C(O)NHEt was administered in a single saline intraperitoneal injection sufficient to provide 40 μg boron per gram body weight to BALB/c mice carrying Harding-Passey melanorna. The results regarding tissue distribution are as follows:

| Hr Post Injection | Boron uptake, μg B per gram tissue | | |
|---|---|---|---|
| | Blood | Brain | Tumor |
| 1 | 54.8 | 45.3 | 51.3 |
| | 54.4 | 39.8 | 48.7 |
| 12 | 0 | 0 | 3.8 |
| | 0 | 0 | 2.8 |

It is evident that some preferential differential concentration of the boron-containing compound in the tumor tissue has occurred. It is to be noted, however, that this uptake is considered inadequate for conventional therapy measured against the standard in clinical use Na$_2$B$_{12}$H$_{11}$SH. The compound of this invention has good solubility and has been found not toxic in BALB/C mice.

We claim:

1. A compound of the formula R$_1$R$_2$NH.BH$_2$C(O)NHR$_3$ wherein R$_1$ and R$_2$ can be the same or different and are H or a lower alkyl, and R$_3$ is a lower alkyl.

2. The compound of claim 1 wherein R$_1$ and R$_2$ are lower alkyl having up to 8 carbon atoms, and R$_3$ is lower alkyl having up to 8 carbon atoms.

3. The compound of claim 1 wherein R$_3$ is ethyl.

4. The compound of claim 2 wherein R$_1$ and R$_2$ are hydrogen.

5. The compound of claim 2 wherein R$_1$ and R$_2$ are methyl.

6. The compound of claim 2 wherein R$_1$ is hydrogen and R$_2$ is methyl.

7. A pharmaceutical composition, for the treatment of an animal having neoplastic tissue, which comprises as the active component a therapeutically effective amount of a compound according to claim 1.

8. The pharmaceutical composition according to claim 7 wherein R$_3$ of said compound is ethyl.

* * * * *